(12) United States Patent
Aguilar et al.

(10) Patent No.: US 11,642,277 B2
(45) Date of Patent: May 9, 2023

(54) VERTICAL DECOMPRESSION RELAXATION DEVICE

(71) Applicant: Bruno Rodrigues Giannoccaro, São Paulo (BR)

(72) Inventors: Naudimar Eloy Aguilar, Seattle, WA (US); Bruno Rodrigues Giannoccaro, São Paulo (BR)

(73) Assignee: FUNCTIONAL PATTERNS HOLDINGS, LLC, Las Vegas, NV (US)

( * ) Notice: Subject to any disclaimer, the term of this patent is extended or adjusted under 35 U.S.C. 154(b) by 565 days.

(21) Appl. No.: 16/628,661

(22) PCT Filed: Jul. 4, 2017

(86) PCT No.: PCT/BR2017/050179
§ 371 (c)(1),
(2) Date: Jan. 4, 2020

(87) PCT Pub. No.: WO2019/006522
PCT Pub. Date: Jan. 10, 2019

(65) Prior Publication Data
US 2020/0214935 A1      Jul. 9, 2020

(51) Int. Cl.
| | | |
|---|---|---|
| *A61L 2/00* | (2006.01) |
| *G01N 21/01* | (2006.01) |
| *A61H 35/00* | (2006.01) |
| *A61H 33/00* | (2006.01) |
| *A61L 2/10* | (2006.01) |
| *A61L 2/20* | (2006.01) |
| *A61L 2/26* | (2006.01) |
| *C02F 1/32* | (2023.01) |
| *C02F 1/78* | (2023.01) |
| *C02F 103/42* | (2006.01) |

(52) U.S. Cl.
CPC ......... *A61H 35/00* (2013.01); *A61H 33/0095* (2013.01); *A61H 33/6005* (2013.01); *A61L 2/10* (2013.01); *A61L 2/202* (2013.01); *A61L 2/26* (2013.01); *C02F 1/325* (2013.01); *C02F 1/78* (2013.01); *A61H 2033/0037* (2013.01); *A61H 2035/004* (2013.01); *A61L 2202/24* (2013.01); *C02F 2103/42* (2013.01); *C02F 2303/04* (2013.01)

(58) Field of Classification Search
CPC ......... A61L 2/10; A61L 2/183; A61L 2202/11
USPC ................................. 422/24; 250/434–435
See application file for complete search history.

(56) References Cited

U.S. PATENT DOCUMENTS 5,807,216 A * 9/1998 Arad ................... A61H 35/00
                                                        482/148
2004/0036034 A1 * 2/2004 Hur ......................... A61L 2/12
                                                        250/435

* cited by examiner

*Primary Examiner* — Monzer R Chorbaji
(74) *Attorney, Agent, or Firm* — D'Ambrosio & Menon, PLLC; Usha Menon

(57) ABSTRACT

Vertical decompression relaxation device with vertical tank, with access ladders, with handrail and stairs for internal access, and tie rods adjustable fasteners to tie rods, mainly in the treatment of muscle and fascia stiffness.

5 Claims, 3 Drawing Sheets

VERTICAL DECOMPRESSION RELAXATION DEVICE

CROSS-REFERENCE TO RELATED APPLICATIONS

Not applicable

STATEMENT REGARDING FEDERALLY SPONSORED RESEARCH OR DEVELOPMENT

Not applicable

THE NAMES OF THE PARTIES TO A JOIN RESEARCH AGREEMENT

Not applicable

Figure 1:
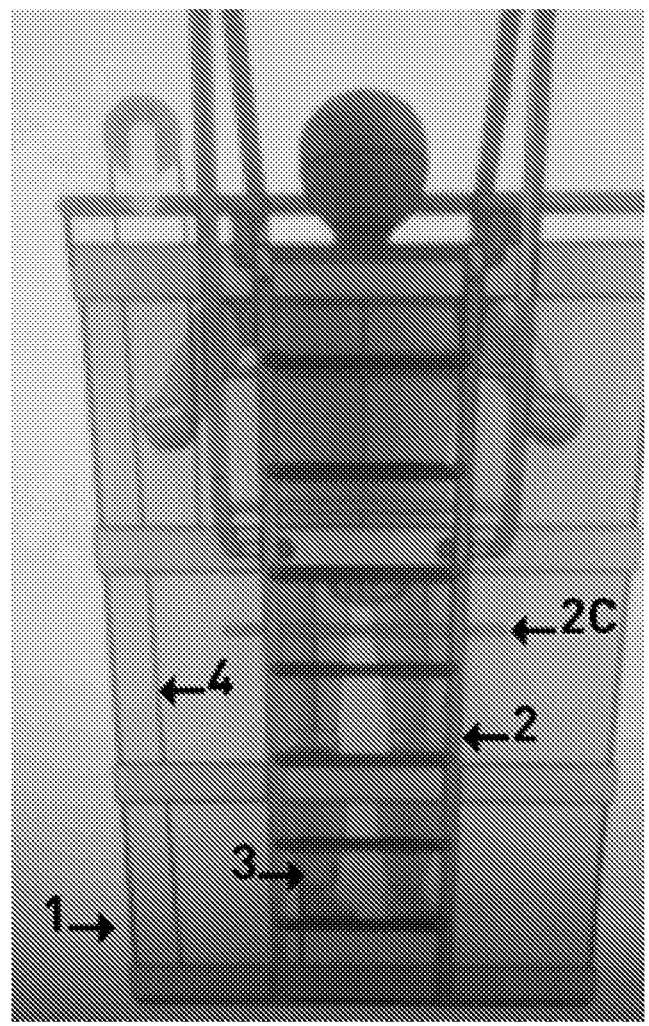

INCORPORATION-BY REFERENCE OF MATERIAL SUBMITTED A READ-ONLY OPTICAL DISC OR A TEXT FILE VIA THE OFFICE ELECTRONIC FILING SYSTEM

Not applicable

STATEMENT REGARDING PRIOR DISCLOSURES BY THE INVENTOR OR A JOINT INVENTOR

Not applicable

The innovation belongs to the field of human needs, specifically physiotherapy, Spas and relaxation, being a vertical decompression relaxation device.

BACKGROUND OF THE INVENTION

Physiotherapy is a health science applied to the study, diagnosis, prevention and treatment of functional kinetic dysfunctions of organs and systems. Its management requires an understanding of the structures and functions of the human body. It studies, diagnoses, prevents, and treats, among others, kinetic-functional disorders (of biomechanics and human functionality) resulting from changes in human organs and systems. It may also have analgesic effects. In addition, physiotherapy studies the beneficial effects of physical resources such as body movement, radiations and electromagnetic currents, ultrasound, among other features resources, on the human body.

FIELD OF THE INVENTION

The muscle-bone concept presented in the usual anatomical description results in a purely mechanical model of motion. It separates movement into discrete functions, without giving a vision of the perfect integration seen in a living body. When a part moves, the body responds as a whole. Functionally, the only tissue to which such a response can be attributed is the connective tissue.

We have as an example of connective tissue the ligaments, joint capsules, tendons and the fasciae. The fascia is a plastic tissue that functions as an envelope for muscles that are an elastic tissue. The muscle being stretched tends to return to its resting length, while the fascia if stretched slowly will deform plastically.

The fascia when placed in tension tends to guide collagen cells along the tension lines that are generated in a given movement. Tension through the fascia stretches the bonds between the molecules. This creates an electrical flow known as piezoelectric charge. This charge can be read by cells in the vicinity of the charge and connective tissue cells are able to respond by increasing, reducing, or changing the intercellular elements in the area. The fascia transmits mechanical information—the interaction between tension and compression—through the collagen fibers of its fibrous network. This fibrous system has a simple form of "push and pull" communication transmitted along the fibers of the fascia and the fundamental substance.

Combined with the highly adaptive characteristic of connective tissue, when the fascia is regularly subjected to an increase in physiological stretching, the fibroblasts of that area adjust their matrix by remodeling the tissue architecture to better respond to the demand of that site. Therefore, with the help of fibroblasts, tissues are slowly but constantly reacting to day-to-day stresses as well as to specific training, reshaping the arrangement of their collagen fiber network. According to Neuberger et al., 1953, in a healthy body half of collagen fibers are replaced each year. Interestingly, the fascial tissues of young people show stronger ripples between their collagen fibers, resembling elastic springs, where in older people the fibers appear quite flattened. A better quality of elastic movement in young people is associated with the bidirectional arrangement of their fascia network. In contrast, with aging and loss of flexibility in our gait, fascial architecture acquires an accidental and multidirectional arrangement of fibers.

Thus, a machine was created that helps to decrease the stresses generated in a single direction of the fascia lines, promoting a decrease in the compressions resulting from the unidirectional movement of the fascia lines.

In the sense of circumventing such problems, the Float or Sensory Deprivation Chamber is presented in the technique, where the patient, in an environment under the deprivation of light and sound, is floated horizontally—lying down—for relaxation.

There is a gap in the art regarding devices that allow vertical fluctuation, thus enabling joint decompression and total relaxation of the individual through the submerged body except his/her head and neck.

DESCRIPTION OF RELATED ART INCLUDING INFORMATION DISCLOSED UNDER 37 CFR 1.97 AND 1.98

Not applicable

BRIEF SUMMARY OF THE INVENTION

Faced with this gap, a vertical tank (1) is hereby proposed, preferably with a capacity of 1500 l, with access stairs (2) to the upper edge, with handrail (2B) and internal access stairs (2C), preferably on the tank body itself, on its internal walls and adjustable tie rods (4)—which will come throughout the treatment to be fixed on the patient's ankles—attached to tie rods (3). It is also equipped with recirculation by means of pumps (5)—at least one—with flotation fluid heating system (6) (not represented) and fluid sterilization system (7) preferably by means of UV and/or ozone rays.

BRIEF DESCRIPTION OF THE SEVERAL VIEWS OF THE DRAWING(S)

The invention can be better understood through the figures.

FIG. 1 is a frontal view of the invention with a patient under treatment.

Figure 2:
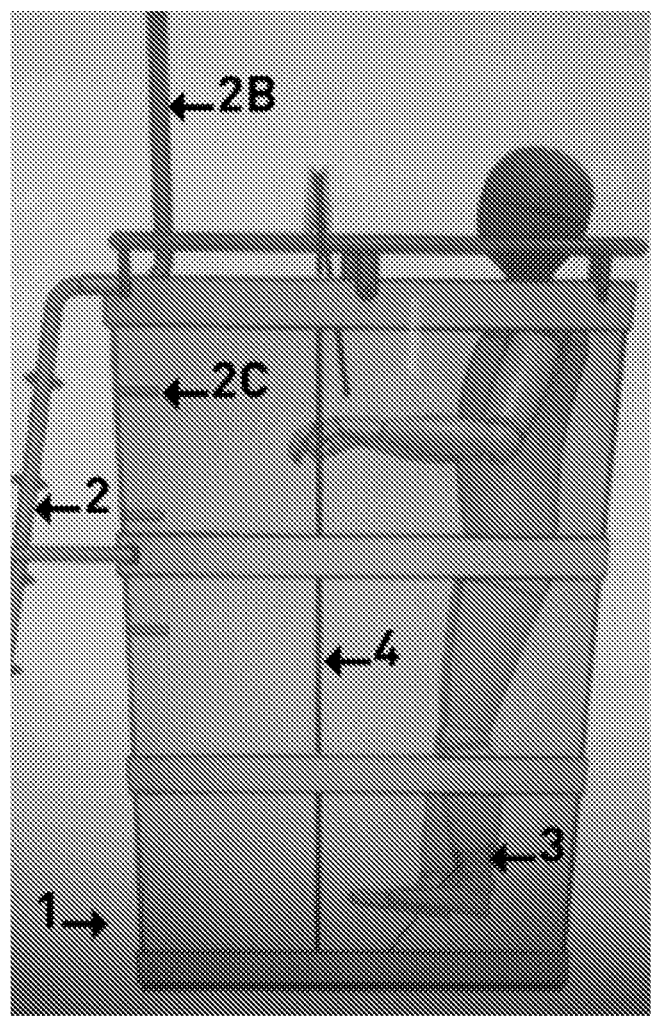

FIG. 2 presents a side cut of the invention with a patient undergoing treatment.

Figure 3:
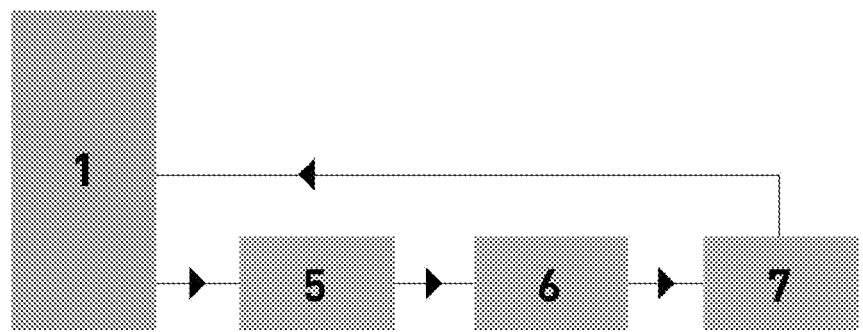

FIG. 3 has a flowchart of the recirculation, heating and sterilization system of the invention.

DETAILED DESCRIPTION OF THE INVENTION

Given its innovative characteristic, it is efficient in the treatment of muscle and fascia stiffness.

In summary, the innovation is a vertical decompression relaxation device with vertical tank (1), with access stairs (2), with handrail (2B) and internal access stairs (2C), and tie rods (4) adjustable fasteners to tie rods (3) with a recirculation, heating and sterilization system, mainly used in the treatment of muscle and fascia stiffness.

This innovation is not limited to the representations commented or illustrated here and should be understood in its broad scope. Many modifications and other representations of innovation will come to the mind of that who is versed in the technique to which this innovation belongs, and the benefit of the teaching presented in the previous descriptions and attached drawings. Furthermore, it is to be understood that innovation is not limited to the specific form revealed, and that modifications and other forms are understood as included within the scope of the attached claims. Although specific terms are used here, they are used only generically and descriptively and not as a limitation purpose.

The invention claimed is:

1. A vertical decompression relaxation device comprising:
a vertical tank, wherein the vertical tank comprises:
access stairs located outside the tank;
internal access stairs arranged within the tank;
a handrail, the handrail encircling an opening of the tank;
a pulley system; and
adjustable fasteners, wherein the adjustable fasteners are configured for attachment to at least a user's ankles, and wherein the adjustable fasteners are coupled to the pulley system.

2. The vertical decompression relaxation device according to claim 1, wherein the vertical tank is configured to recirculate a fluid using least one pump.

3. The vertical decompression relaxation device according to claim 2, wherein the tank further comprises:
a heating system for the recirculating fluid; and
a system for sterilizing the fluid.

4. The vertical decompression relaxation device according to claim 3, wherein the sterilization of the fluid is performed using UV rays.

5. The vertical decompression relaxation device according to claim 3, wherein the sterilization of the fluid is performed using ozone.

* * * * *